(12) United States Patent
Vecchio et al.

(10) Patent No.: US 9,551,008 B2
(45) Date of Patent: Jan. 24, 2017

(54) TOMATO PLANTS WITH INTENSE PHENOTYPE AND TYLCV RESISTANCE

(71) Applicant: NUNHEMS B.V., Nunhem (NL)

(72) Inventors: Franco Vecchio, Fidenza (IT); Henk Verbakel, Boekel (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 14/385,151

(22) PCT Filed: Mar. 12, 2013

(86) PCT No.: PCT/EP2013/055044
§ 371 (c)(1),
(2) Date: Sep. 13, 2014

(87) PCT Pub. No.: WO2013/135726
PCT Pub. Date: Sep. 19, 2013

(65) Prior Publication Data
US 2015/0047067 A1   Feb. 12, 2015

Related U.S. Application Data

(66) Substitute for application No. 61/611,749, filed on Mar. 16, 2012.

(30) Foreign Application Priority Data

Mar. 16, 2012 (EP) .................................... 12159860

(51) Int. Cl.
| | |
|---|---|
| *A01H 5/08* | (2006.01) |
| *A01H 1/00* | (2006.01) |
| *C12N 15/82* | (2006.01) |
| *A01H 1/04* | (2006.01) |
| *A01H 5/00* | (2006.01) |
| *A01H 1/02* | (2006.01) |
| *C12N 15/00* | (2006.01) |

(52) U.S. Cl.
CPC ............. *C12N 15/8283* (2013.01); *A01H 1/02* (2013.01); *A01H 1/04* (2013.01); *A01H 5/00* (2013.01); *A01H 5/08* (2013.01); *C12N 15/8261* (2013.01)

(58) Field of Classification Search
None
See application file for complete search history.

(56) References Cited

PUBLICATIONS

Gonzalez-Cabezuelo et al., "Genotyping Selection for Resistance Against Tomato Yellow Leaf Curl Virus (TYLCV) Conferred by Ty-1 and Ty-3 Genes in Tomato", Molecular Breeding, (2012), DOI 10.1007/s11032-012-9701-3.
Ji, Y. et al., "Ty-3, A Begomovirus Resistance Locus Near the Tomato Yellow Leaf Curl Virus Resistance Locus Ty-1 on Chromosome 6 of Tomato", Springer, (2007), vol. 20, pp. 271-284.
Lapidot, M. et al., "Development of a Scale for Evaluation of Tomato Yellow Leaf Curl Virus-Resistance Level in Tomato Plants", APS journals, (2006), vol. 96, pp. 1404-1408.
Lin, L. et al., "De Novo Assembly of Potential Linear Artificial Chromosome Constructs Capped with Expansive Telomeric Repeats", BioMed Central, (2011), vol. 7, p. 10.
Zamir, D., et al., "Mapping and introgression of a tomato yellow leaf curl virus tolerance gene, Ty-1", Theoretical and Applied Genetics, (1994), Springer, vol. 88, pp. 141-146.
Michelson, I. et al. "Accumulation and Translocation of Tomato Yellow Leaf Curl Virus (TYLCV) in a Lycopersicon Esculentum Breeding Line Containing the L. chilense TYLCV Tolerance Gene Ty-1", APS journals, (1994), vol. 84, pp. 928-933.
Nunhems Website, Product Leaflet, XP55032008, (2010).
Verlaan, M., et al., "Chromosomal Rearrangements between Tomato and Solanum Chilense Hamper Mapping and Breeding of the TYLCV Resistance Gene Ty-1", Plant Journal, (2011), vol. 68, No. 6, pp. 1093-1103.
Yu, W., et al., "Engineered Minichromosomes in Plants", Current Opinion in Biotechnology, ScienceDirect, (2007), vol. 18, pp. 425-431.
Hutton S.F., et al., "Fine Mapping of a Begomovirus Resistance Gene in Tomato", Proceedings of the Plant & Animal Genomes XVIII Conference, CA, USA: San Diego, (2010), p. 204 (abstract).
Ausubel, F.M. (Ed.) et al., "Current Protocols in Molecular Biology", (1994), vol. 1 and 2 Current Protocols, Wiley (voluminous book).
R.D.D. Croy (Ed.) "Plant Molecular Biology Labfax" (1993), BIOS Scientific Publications Ltd., Oxford, UK (voluminous book).
Sambrook, M.R. and Russell, J. (Eds.), "Molecular Cloning: A Laboratory Manual", (2001), Third Edition, Cold Spring Harbor Laboratory Press, NY (voluminous book).
Sambrook, M.R. and Russell, J. (Eds.), "Molecular Cloning: A Laboratory Manual", (1989), Second Edition, Cold Spring Harbor Laboratory Press, NY (voluminous book).
Allard, R. W., "Principles of Plant breeding", (1999), Second Edition, J. Wiley, New York (ISBN 0-471-02309-4) (voluminous book).
PCTEP2013055044 International Search Report and Written Opinion, dated Apr. 26, 2013.

*Primary Examiner* — Phuong Bui
(74) *Attorney, Agent, or Firm* — McBee Moore Woodward Vanik IP LLC (57) ABSTRACT

The present invention relates to the field of tomato plants having an intense phenotype and Tomato Yellow Leaf Curl Virus (TYLCV) resistance.

12 Claims, 4 Drawing Sheets

TOMATO PLANTS WITH INTENSE PHENOTYPE AND TYLCV RESISTANCE

CROSS REFERENCE TO RELATED APPLICATIONS

This application is a §371 National Stage Application of PCT/EP2013/055044, filed Mar. 12, 2013, which claims priority to EP 12159860.1, filed Mar. 16, 2012 and to U.S. Provisional Application No. 61/611,749, filed Mar. 16, 2012.

BACKGROUND

Field of the Invention

The present invention relates to the field of plant breeding, in particular tomato breeding. The invention provides for the genetic combination of the recessive gene conferring the "intense" phenotype and the (partially) dominant Ty-1 resistance gene (or Ty-3, or orthologs of Ty-1 or Ty-3), conferring resistance towards Tomato Yellow Leaf Curl Virus (TYLCV). In particular, the combination of the recessive intense allele and the Ty-1 allele (or Ty-3 allele, or orthologs of Ty-1 or Ty-3) on a single chromosome of *Solanum lycopersicum* (chromosome 6 of tomato) in cis configuration is provided, as are tomato plants comprising such a recombinant chromosome in their genome. Also provided are seeds from which such plants can be grown, plant parts, cells, tissues or organs of such plants and breeding methods for transferring the recombinant chromosome 6 comprising intense and Ty-1 (or intense and Ty-3, or intense and orthologs of Ty-1 or Ty-3) in cis configuration to other cultivated tomato plants or plant cells.

BACKGROUND OF THE INVENTION

Description of Related Art

Tomato yellow leaf curl virus (TYLCV) is a Begomovirus (a genus within the Geminiviridae) transmitted by the sweet potato white flies (*Bemisia tabaci*), which causes serious losses in tomato production areas throughout the world. TYLCV has a large host range, including tomato, tobacco, potato and pepper. Infection leads to stunting, yellowing, leaf curling and flower abortion. No resistance has been found in the cultivated tomato germplasm, *Solanum lycopersicum*, itself. However, resistance-conferring chromosomal regions have been introgressed into *Solanum lycopersicum* from wild relatives of tomato and introgression segments have been mapped. To date five resistance genes have been mapped, referred to as Ty-1 to Ty-5.

A number of commercial tomato varieties have on chromosome 6 a large introgression fragment from *Solanum chilense* accession LA1969, on which the Ty-1 resistance gene is located. The *S. chilense* introgression fragment is very large, about 30 million base pairs (30 Megabases or Mega base pairs, 30 Mb) and covers most of the short arm, the centromere and part of the long arm of chromosome 6, as for example visualized using Fluorescent in situ hybridization (FISH) images (FIG. 3 of Verlaan et al. 2011, Plant Journal 68: 1093-1103).

The location of the Ty-1 gene on the introgressed segment has been mapped in several mapping populations, in order to identify the exact location of the Ty-1 gene on chromosome 6, with the aim to reduce the size of the *S. chilense* introgression fragment and negative traits (linkage drag) which may be located on the introgression fragment.

Ty-1 was first mapped to the pericentromere of tomato chromosome 6 by Zamir et al. (1994, TAG 88: 141-146) near molecular marker TG97. However, later mapping studies gave contradictory results regarding the location of Ty-1 on the *S. chilense* introgression fragment. In 2011 Verlaan et al. (supra) showed that efforts to precisely locate Ty-1 on the *S. chilense* fragment failed previously because of low marker coverage combined with severe recombination suppression in the Ty-1 region. Using physical mapping of BACs (Bacterial Artificial Chromosomes) to the Ty-1 region of chromosome 6 and development of CAPS markers (Cleaved Amplified Polymorphic Sequence markers) for these BACs, they were able to map the location of Ty-1 to the long arm of chromosome 6, between CAPS markers MSc05732-14 and MSc05732-4 (spanning a region of about 600 kb (kilobases or kilo base pairs).

Verlaan et al. (2011, supra) also refer to Ty-3, a TYLCV resistance gene located on *S. lycopersicum* chromosome 6 on an introgression fragment from *S. chilense* accession LA2779 (or LA1932). They found that the mapped Ty-1 region overlaps partially with the region where Ty-3 has been mapped, between markers T0774 and cLEG-31-P16 (Hutton et al. 2010, Proceedings of Plant and Animal Genomes XVIII Conference CA, USA, San Diego, p. 204) and suggest that Ty-1 and Ty-3 may in fact be allelic, i.e alleles of the same TYLCV resistance gene, located on the long arm of chromosome 6.

Intense™ tomato varieties, such as commercial varieties NUN 3155 TO F1 and NUN 3362 TO (Nunhems B.V.) comprise a mutation in an unknown gene (of which also the location in the genome was unknown), which converts the locular gel found in the seed cavities of tomato fruits into fleshy tissue. To see this "intense phenotype" the mutation needs to be present in homozygous form, i.e. the intense allele which confers the intense phenotype is recessive. As the mutant intense allele is present in the cultivated *S. lycopersicum* genome, which has a low degree of polymorphism in many genomic regions, it is difficult to map the responsible gene.

Many attempts of the inventors to combine the wild TYLCV resistance gene Ty-1 with the intense phenotype of cultivated tomato failed, indicating that the mutant intense allele is located on the same chromosome as the Ty-1 allele and may very likely not be combinable with Ty-1, due to recombination suppression and/or chromosomal rearrangements. The Ty-1 allele is found on a very large wild introgression fragment (about 30 Mb) and has neither been fine-mapped, nor has the wild introgression size been reduced, due to the severe suppression of recombination around the Ty-1 introgression region. The exact cause of the severe suppression of recombination is unknown, but it was speculated in Verlaan et al. (2011, Plant J 68: 1093-1103) on page 1094 (RH Column last paragraph) that the location of the Ty-1 gene in pericentromeric heterochromatin regions and/or chromosomal rearrangements between cultivated and wild tomatoes may play a role. They also show that this severe recombination suppression is not population specific (page 1096) and that Ty-1 may be allelic with Ty-3, or very closely linked.

SUMMARY

It is an object of the invention to provide a *Solanum lycopersicum* plant comprising an intense phenotype and a TYLCV resistance phenotype.

DETAILED DESCRIPTION OF A PREFERRED EMBODIMENT

The indefinite article "a" or "an" does not exclude the possibility that more than one of the element is present, unless the context clearly requires that there be one and only one of the elements. The indefinite article "a" or "an" thus usually means "at least one".

As used herein, the term "plant" includes the whole plant or any parts or derivatives thereof, such as plant organs (e.g., harvested or non-harvested storage organs, tubers, fruits, leaves, seeds, etc.), plant cells, plant protoplasts, plant cell or tissue cultures from which whole plants can be regenerated, plant calli, plant cell clumps, and plant cells that are intact in plants, or parts of plants, such as embryos, pollen, ovules, ovaries, fruits (e.g., harvested tissues or organs, such as harvested tomatoes or parts thereof), flowers, leaves, seeds, tubers, bulbs, clonally propagated plants, roots, root-stocks, stems, root tips and the like. Also any developmental stage is included, such as seedlings, immature and mature, etc.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"F1, F2, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "gene" means a DNA sequence comprising a region (transcribed region), which is transcribed into a messenger RNA molecule (mRNA) in a cell, and an operably linked regulatory region (e.g. a promoter).

The term "locus" (loci plural) means a specific place or places or a site on a chromosome where for example a gene or genetic marker is found. The intense locus is thus the location in the genome where the intense gene is found on chromosome 6 of the tomato genome. Likewise the Ty-1 locus (or Ty-3 locus) is the *S. chilense* locus where the Ty-1 gene (or Ty-3 gene) is found on chromosome 6 (either on chromosome 6 of the *S. chilense* genome or on the introgressed fragment of chromosome 6 of the tomato genome). The Ty-1 or Ty-3 orthologous loci can be found at essentially the same position on chromosome 6 of wild *Solanum* relatives of tomato.

"Genetic distance" between loci on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Introgression fragment" or "introgression segment" refers to a chromosome fragment (or part) which has been introduced into another plant of the same or related species by crossing or traditional breeding techniques. In tomato, wild relatives of tomato are often used to introgress fragments of the wild genome into the genome of cultivated tomato, *S. lycopersicum*. Such a cultivated tomato plant thus has a "genome of *S. lycopersicum*", but comprises in the genome a fragment of a wild relative of tomato, e.g. an introgression fragment of a related wild species'genome, such as *Solanum chilense* or another wild relative of tomato. It is understood that the term "introgression fragment" never includes a whole chromosome, but only a part of a chromosome.

Figure 3:
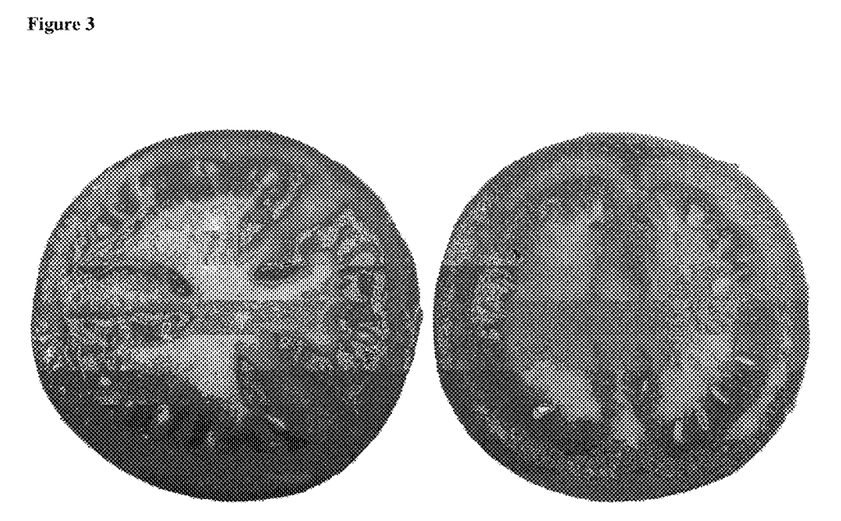
FIG. 3: Photograph of a cut-open tomato fruit having the intense phenotype (right) and a fruit having the normal fruit phenotype (left).

"Intense allele" (or "Int") or "intense allele" (or "i") refers herein refers to the *S. lycopersicum* allele conferring a "normal fruit phenotype" (Int) or an "intense phenotype" (i), respectively. The Intense allele is dominant, i.e. it is the allele which, when present in the genome in one (heterozygous) or two (homozygous) copies confers normal tomato fruits, having normal seed cavities, i.e. with gel around the seeds (locular gel). Tomato fruits having a "normal fruit phenotype" thus refer to fruits which have locular gel, as shown for example in FIG. 3, left side. The intense allele is recessive, i.e. only when the dominant Intense allele is lacking from the genome is the intense phenotype seen. Thus Intense/Intense (Int/Int) plants and Intense/intense (Int/i) plants have a normal fruit phenotype, while homozygous intense/intense (i/i) plants have an "intense fruit phenotype", as shown e.g. in FIG. 3, right side (see further below).

The "Ty-I allele" refers to a TYLCV resistance conferring allele, or a resistance conferring part thereof, originally introgressed into cultivated tomato (onto *S. lycopersicum* chromosome 6) from *Solanum chilense* (previously referred to as *Lycopersicon chilense*), in particular from *S. chilense* accession LA1969. The term "Ty-1 allele" thus also encompasses Ty-1 alleles obtainable from other TYLCV resistant *S. chilense* accessions. When one or two Ty-I alleles is/are present in the genome, the plant is resistant against TYLCV, i.e. has a TYLCV resistance phenotype. In cultivated tomato lacking the *S. chilense* introgression fragment, the *S. lycopersicum* allele found at the same locus is herein referred to as "+" allele. Thus Ty-1/Ty-1 plants and Ty-1/+ plants show a TYLVC resistance phenotype, whereas +/+ plants are plants which lack the Ty-1 allele and lack the TYLCV resistant phenotype conferred by the Ty-1 allele (i.e. are susceptible to TYLCV). The "Ty-3 allele" refers to a TYLCV resistance conferring allele, or a resistance conferring part thereof, originally introgressed into cultivated tomato (onto chromosome 6 of *S. lycopersicum*) from *Solanum chilense* (previously referred to as *Lycopersicon chilense*), in particular *S. chilense* accession LA2779 or LA1932. The term "Ty-3 allele" thus also encompasses Ty-3 alleles obtainable from other TYLCV resistant *S. chilense* accessions, which alleles can be introgressed onto tomato chromosome 6. When one or two Ty-3 alleles is/are present in the genome, the plant is resistant against TYLCV, i.e. has a TYLCV resistance phenotype.

"Ty-1 or Ty-3 orthologous alleles" or "Ty-1 or Ty-3 orthologs" are alleles of Ty-1 and Ty-3 resistance genes present in other wild relatives of tomato, on the orthologous chromosomes 6, at the equivalent locus where the Ty-1 and Ty-3 alleles are found in *S. chilense*. Such ortholgous alleles may thus be found on chromosome 6 of wild relatives of *S. lycopersicum*, such as *S. peruvianum, S. pimpinellifolium, S. habrochaites, S. cheesmaniae* and others and are transferable, by introgression, onto *S. lycopersicum* chromosome 6.

The "intense phenotype" or "intense fruit phenotype" is the phenotype conferred by the presence of two mutant *Solanum lycopersicum* intense alleles in the genome, whereby the homozygous intense alleles (intense/intense) cause the locular gel found in the seed cavities of tomato fruits to become fleshy tissue. The mature tomato fruits therefore have essentially no gel in the seed cavities surrounding the seeds and the locular gel is replaced by fleshy tissue. The intense phenotype is depicted e.g. in FIG. 3, fruit on the right.

The "normal fruit phenotype" refers to the tomato fruits comprising gel in the seed cavities (locular gel), due to the presence of a *S. lycopersicum* Intense allele, either in homozygous or heterozygous form (Intense/Intense or Intense/intense). The normal fruit phenotype is depicted e.g. in FIG. 3, fruit on the left.

A "TYLCV resistance phenotype" or "TYLCV resistance" refers to resistance against TYLCV conferred by the *S. chilense* Ty-1 allele and/or Ty-3 allele (or orthologs of Ty-1 or Ty-3) when present in the tomato genome in one or two copies. The TYLCV resistance phenotype and the presence of the Ty-1 allele and/or Ty-3 allele (or orthologs of Ty-1 or Ty-3) can be tested using the "TYLCV resistance assay" and/or the Ty-1 or Ty-3 marker assays (or Ty-1 or Ty-3 ortholog marker assays). A "+" may herein be used to designated the *S. lycopersicum* allele on chromosome 6 at the locus where otherwise the Ty-1 or Ty-3 alleles (or Ty-1 or Ty-3 orthologous alleles) are found.

A "TYLCV resistance assay" can be carried out in different ways, either as an artificial inoculation assay or as a field test, as also described elsewhere herein or as commonly known in the art. In the artificial inoculation assay preferably tomato seedlings (e.g. first true leaf stage or 2-3 leaf stage) are exposed to viruliferous whiteflies (*Bemisia tabaci* biotype B carrying TYLCV) and disease symptoms are assessed about 21 or 30 days after exposure to whiteflies on a scale of 0 (no visible symptoms), 1 (very slight yellowing of leaflet margins on inoculated plants), 2 (some yellowing and minor curling of leaflet ends), 3 (a wide range of leaf yellowing, curling and cupping) to 4 (severe plant stunting and yellowing). See e.g. Lapidot et al. 2006, Phytopathology 96, No. 12, page 1405; or Ji et al. 2007, Mol. Breeding 20: 271-284, page 273. A plant of a particular genotype is considered to be TYLCV resistant if the average disease score of a plurality of plants of that genotype is significantly lower compared to the susceptible controls (plants lacking an introgression fragment comprising Ty-1 or Ty-3 or an Ty-1 or Ty-3 ortholog, such as cultivar Moneymaker).

The "Ty-1 marker assay" is a molecular marker assay which can be used to test whether on tomato chromosome 6 an introgression from *S. chilense* comprising the Ty-1 allele is present in the genome, e.g. using one or more markers selected from cLEG-31-P16, Msc05732-4 or any *S. chilense*-genome specific marker between cLEG-31-P16 and Msc05732-4. In some embodiments one or more markers are used selected from the group consisting of Msc05732-14, Msc05732-4, or any *S. chilense*-genome specific marker between Msc05732-14 and Msc05732-4.

The "Ty-3 marker assays" is a molecular marker assay which can be used to test whether on tomato chromosome 6 an introgression from *S. chilense* comprising the Ty-3 allele is present in the genome, e.g. using one or more markers selected from cLEG-31-P16, Msc05732-4, or any *S. chilense*-genome specific marker between cLEG-31-P16 and Msc05732-4. In some embodiments one or more markers are used selected from the group consisting of cLEG-31-P16, T0774, or any *S. chilense*-genome specific marker between cLEG-31-P16 and T0774, such as MSc05732-4, MSc05732-3, M-M082G10, or others.

A "Ty-1 or Ty-3 ortholog marker assay" is a molecular marker assay which can be used to test whether on tomato chromosome 6 an introgression comprising a Ty-1 or Ty-3 orthologous allele from a wild relative of tomato comprising the Ty-1 or Ty-3 orthologous allele is present in the genome.

"Tomato plants" or "cultivated tomato plants" are plants of the *Solanum lycopersicum*, i.e. varieties, breeding lines or cultivars of the species *Solanum lycopersicum*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species. The so-called heirloom varieties or cultivars, i.e. open pollinated varieties or cultivars commonly grown during earlier periods in human history and often adapted to specific geographic regions, are in one aspect of the invention encompassed herein as cultivated tomato plants.

Tomato and the wild relatives of tomato is/are diploid and has/have 12 pairs of homologous chromosomes, numbered 1 to 12. "Tomato chromosome 6" refer to the *Solanum lycopersicum* chromosome 6, as known in the art. "Orthologous chromosome 6" refers to the chromosome 6 of wild relatives of tomato, parts of which can be introgressed into tomato chromosome 6.

"Wild relatives of tomato" include *S. arcanum, S. chmielewskii, S. neorickii* (=*L. parviflorum*), *S. cheesmaniae, S. galapagense, S. pimpinellifolium, S. chilense, S. corneliomulleri, S. habrochaites* (=*L. hirsutum*), *S. huaylasense, S. sisymbriifolium, S. peruvianum, S. hirsutum* or *S. pennellii*.

"Average" refers herein to the arithmetic mean.

"In coupling phase" or "in coupling configuration" or "in cis" refers to the genetic condition in which the alleles of two different loci are genetically and physically linked together as a unit on one chromosome and inherit together as a unit. Preferably the loci are in close proximity to one another, reducing the likelihood that they will be separated again by recombination.

A "recombinant chromosome" refers to a chromosome having a new genetic makeup arising through crossing over between homologous chromosomes, e.g. a "recombinant chromosome 6", i.e. a chromosome 6 which is not present in either of the parent plants and arose through a rare crossing-over event between homologous chromosomes of a chromosome 6 pair. Herein, for example, a recombinant tomato chromosome 6 comprising Ty-1 and intense in coupling phase (in cis) and a recombinant tomato chromosome 6 comprising Ty-3 and intense in coupling phase (in cis) is provided, as is a recombinant tomato chromosome 6 comprising a Ty-1 or Ty-3 orthologous allele and intense in coupling phase (in cis).

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a recombinant chromosome 6 can be obtained and/or transferred.

The present invention relates to *Solanum lycopersicum* plant comprising a TYLCV resistance phenotype and an intense fruit phenotype, wherein said plant comprises at least one recombinant chromosome 6 comprising the recessive intense allele and an introgression fragment (from a wild relative of tomato) comprising an allele conferring TYLCV resistance in coupling configuration. Preferably the *Solanum lycopersicum* plant is a non-transgenic plant, e.g. a plant obtainable by traditional breeding methods.

It was found that the recessive intense phenotype can be combined with TYLCV resistance conferred through introgression fragments, on chromosome 6 of the *Solanum lycopersicum* genome, derived from wild relatives of tomato, such as *S. chilense*, encoding TYLCV resistance genes, such as Ty-1 or Ty-3. Ty-1 and Ty-3 are likely alleles at the same TYLCV resistance locus on chromosome 6 (Verlaan et al. 2011, supra).

*Solanum lycopersicum* plants with introgression fragments from *S. chilense* Ty-1 and Ty-3 alleles already exist in the art. For example commercial hybrid varieties Anastasia and Boludo (Seminis Vegetable Seeds) comprise a large introgression fragment from *S. chilense* accession LA1969, which comprises the Ty-1 allele. Also non-commercial breeding lines comprising introgression fragments derived from *S. chilense* chromosome 6, comprising Ty-1 or Ty-3 alleles, exist in the art, such as LA1932-AL-F2 comprising a large *S. chilense* introgression fragment (about 27 cM) which comprises the Ty-3 allele and LA1931-AL-F2, which comprises a much smaller *S. chilense* introgression fragment (about 6 cM) comprising Ty-3 (see Ji et al. 2007, Mol. Breeding 20: 271-284).

Although the current sources of Ty-1 and Ty-3 introgressions are limited to three sources (*S. chilense* accessions LA1969 from Peru, LA1932 from Peru and LA2779 from Chile), there are probably many other wild *Solanum* accessions which comprise Ty-1 or Ty-3 alleles or ortholgous alleles at the same locus on chromosome 6. Such Ty-1 or Ty-3 alleles can also be combined with the intense allele as described herein, to generate a recombinant chromosome 6 comprising a Ty-1 or T-3 allele or orthologous allele in coupling phase with the recessive intense allele.

Figure 4:
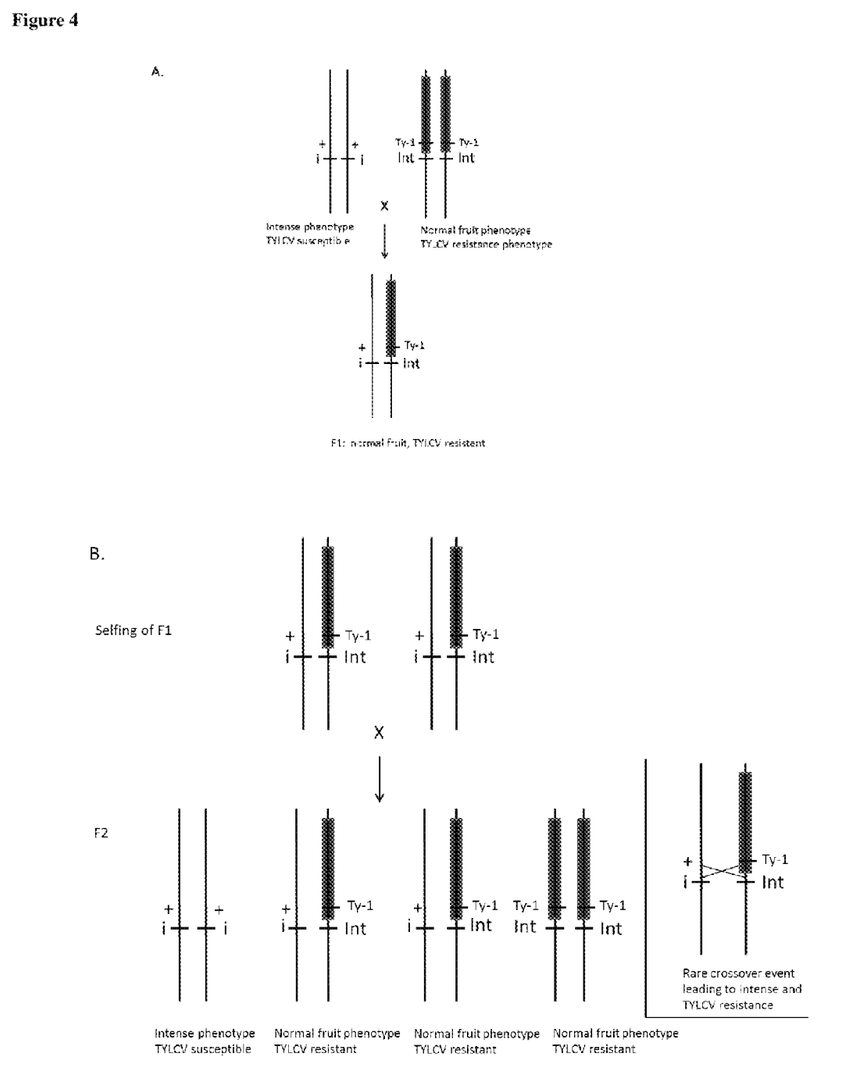
FIG. 4: Schematic illustration of a crossing scheme which can be used to identify rare recombinant plants comprising the intense fruit phenotype and TYLCV resistance.

Accessions of wild tomato relatives, such as accessions obtainable from the TGRC (Tomato Genetic Resource Center) or other seed collections, can be screened for TYLCV resistance using phenotypic and/or Ty-1 and/or Ty-3 markers assays, and/or Ty-1 or Ty-3 ortholog marker assays, and resistant accessions can be crossed with a *Solanum lycopersicum* plant comprising an intense allele in heterozygous or homozygous form. The F2 generation (or further generation, such as the F3 or a backcross generation) can then be screened for recombinant plants having the combination of TYLCV resistance and the intense fruit phenotype. This combination will only be found if the *Solanum lycopersicum* chromosome 6 (comprising the intense allele) has recombined with the chromosome 6 comprising the Ty-1 or Ty-3 allele or orthologous Ty-1 or Ty-3 allele. See for example FIGS. 4 A and B.

In one embodiment a tomato plant is provided comprising a recombinant chromosome 6, comprising a Ty-1 or Ty-3 allele (or orthologous allele) coupled in cis with the intense allele and wherein the plant has a TYLCV resistance phenotype and an intense phenotype.

In one aspect the TYLCV resistance locus and the intense locus are in close proximity to each other, i.e. the genetic distance and the physical distance between the loci is preferably low. In one embodiment the genetic distance between the TYLCV resistance locus and the intense locus is preferably 5 cM or less, such as equal to or less than 4 cM, 3 cM, 2 cM, 1 cM, 0.5 cM, 0.25 cM, 0.1 cM, 0.05 cM, 0.01 cM, 0.001 cM or less. In one embodiment the physical distance between the TYLCV resistance locus and the intense locus is preferably less than 10 Mb, such as equal to or less than 7 Mb, 6 Mb, 5 Mb, 4 Mb, 3 Mb or less.

In a first embodiment a tomato plant is provided which comprises an intense phenotype, conferred by an intense allele on each of the homologous chromosomes 6 (i.e. the plant is homozygous for the intense allele), and TYLCV resistance conferred by an introgression fragment on chromosome 6, wherein the introgression fragment is derived from a wild relative of tomato and wherein the introgression fragment comprises a Ty-1 or Ty-3 resistance allele, or a Ty-1 or Ty-3 orthologous resistance allele. In one embodiment the introgression fragment on chromosome 6 comprising the Ty-1 or Ty-3 allele and is derived from *S. chilense*. In a specific embodiment the introgression fragment is derived from an *S. chilense* accession selected from accession LA1969, LA1932 and LA2779 (available from TGRC). In a different embodiment the introgression fragment is derived from an orthologous chromosome 6, such as from a TYLCV resistant accession of a wild relative of tomato, such as *S. peruvianum*. In one specific embodiment the introgression fragment is the *S. chilense* fragment found in seeds deposited under accession number NCIMB 41930, or a resistance conferring part thereof.

Figure 1:
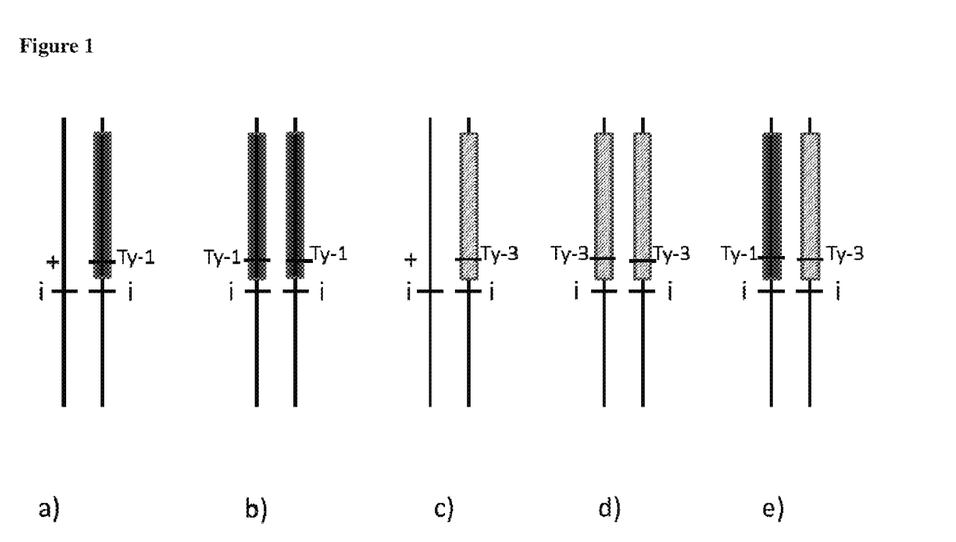

FIGS. 1 *a*) to *e*) illustrates schematically the chromosome 6 pairs which may be present in the different tomato plants which have an intense phenotype (conferred by the intense allele on both chromosomes 6 of the pair) and a TYLCV resistance phenotype conferred by an introgression fragment comprising a Ty-1 allele, or Ty-3 allele, or a Ty-1 or Ty-3 orthologous allele. This Figure illustrates recombinant chromosomes 6 comprising introgression fragments from *S. chilense*, which carry the Ty-1 or Ty-3 allele. However, it is understood that (throughout this specification) embodiments which refer to *S. chilense* introgression fragments equally refer to introgression fragments on tomato chromosome 6 from other wild tomato relatives of tomato, comprising Ty-1 or Ty-3 orthologous alleles on the introgression fragments.

In one embodiment a tomato plant is provided which comprises one recombinant chromosome 6, with Ty-1 or Ty-3 and intense in cis configuration, and the other chromosome 6 with the intense allele only, i.e. without an *S. chilense* (or other wild relative of tomato) introgression fragment on the homologous chromosome 6, as illustrated in FIGS. 1 *a*) and *c*). The other chromosome 6 is thus of *S. lycopersicum* origin entirely. Such a *S. lycopersicum* chromosome 6, comprising the intense allele but lacking a TYLCV-resistance conferring introgression from a wild relative of tomato, is found in Intense™ varieties sold by Nunhems B.V. and in NCIMB 41930. Also a recombinant chromosome 6 comprising an introgression fragment from *S. chilense*, wherein said introgression fragment comprises the Ty-1 allele, in coupling phase with the intense allele is found in NCIMB 41930. The combination of Ty-1 and intense is therefore obtainable by/can be obtained by crossing a tomato plant grown from NCIMB 41930 with another tomato plant.

In one embodiment a tomato plant is provided which comprises two homologous recombinant chromosomes 6, each with the intense and Ty-1 allele in cis configuration, as illustrated in FIG. 1 *b*) or each with the intense and Ty-3 allele in cis configuration, as illustrated in FIG. 1 *d*). In one embodiment the two homologous recombinant chromosomes 6 are identical, whereby the introgression fragments are of the same size and origin and comprise the same TYLCV resistance conferring allele and the same intense allele. A tomato plant with such identical chromosomes can be generated by selfing and selecting homozygous progeny plants. In another embodiment the two homologous recombinant chromosomes may be different, e.g. one may comprise a shorter introgression fragment than the other.

In a further embodiment a tomato plant is provided which comprises two homologous recombinant chromosomes 6, one with the intense and Ty-1 allele in cis configuration and the other one with the intense and Ty-3 allele in cis configuration, as illustrated in FIG. 1 e).

In a preferred embodiment the above tomato plants are F1 hybrids, produced by crossing two parent plants, P1 and P2 each being homozygous for one of the chromosomes 6 shown in any of FIGS. 1 a) to e). Thus, for example, to produce the F1 hybrid comprising the recombinant chromosome of FIG. 1 a), a tomato variety which has the intense phenotype (such as NUN 3155 TO) may be a first parent that is crossed with second parent, said second parent being a tomato plant which is homozygous for the recombinant chromosome 6 (i.e. comprises an intense phenotype and TYLCV resistance conferred by the Ty-1 introgression fragment) and the F1 seeds (from which F1 hybrids according to FIG. 1 a) can be grown) are then collected from that cross.

The tomato plants according to the invention comprise an intense phenotype (conferred by the presence of the homozygous intense allele) and a TYLCV resistance phenotype (conferred by the Ty-1 or Ty-3 allele, or Ty-1 or Ty-3 ortholog, on the introgression fragment).

Tomato plants having the intense phenotype and the TYLCV resistance phenotype can be generated by crossing a tomato plant (Solanum lycopersicum) comprising the intense allele or, preferably, comprising the intense phenotype (i.e. homozygous for the intense allele; see FIG. 4 A) with a plant comprising TYLCV resistance conferred by a Ty-1 or Ty-3 allele (or orthologous allele) on chromosome 6 and selecting recombinant plants in the progeny generations which have both the intense phenotype and the TYLCV resistance phenotype. The coupling of intense and TYLCV resistance in cis can be confirmed by marker analysis and/or by complete co-inheritance of the two phenotypes in progeny generations, e.g. in generations produced by selfing the selected plant or by crossing the selected plant with another tomato plant, said other tomato plant preferably having an intense phenotype.

Plants having the intense phenotype are commercially available, e.g. varieties sold by Nunhems B.V. under the trade name Intense™. Also plants grown from the seeds deposited herein under accession number NCIMB 41930 have the intense phenotype. The phenotype is easily recognized and selected for by allowing mature tomato fruits to develop, cutting these in half and visually determining whether the phenotype is "intense" or "normal", i.e. essentially without gel in the seed cavities or with gel in the seed cavities of the fruit, as seen e.g. in FIG. 3 (the right fruit has the "intense phenotype" and left fruit has a "normal phenotype", i.e. a non-intense phenotype). It is noted that the development of air-cavities ("puffy" fruit) can also develop in intense fruits. Puffy-ness is a problem caused by factors affecting fruit set (such as temperature). Yet, the intense fruit will be equally easy be distinguishable from the normal fruit phenotype, as no locular gel is present. "Essentially no gel" or "essentially without gel" in the seed cavities means in one aspect that the tomato fruits comprise on average seed cavities with at least 98% fleshy tissue and at most 2% gel, more preferably at least 99% fleshy tissue and at most 1% locular gel, most preferably 100% fleshy tissue and no locular gel.

Plants comprising TYLCV resistance conferring alleles on chromosome 6 can for example be Solanum lycopersicum plants comprising an S. chilense introgression fragment on chromosome 6, such as Boludo F1, Anastasia F1, inbred line Ty52 (Michelson et al. 1994, Phytopathology 84, 928-933), plants grown from seed deposited under NCIMB 41930 (all comprising Ty-1 from S. chilense LA1969) or LA1932-AL-F2 or LA1931-AL-F2 (comprising Ty-3 from S. chilense LA1932 and LA1931, respectively), or others. Alternatively plants comprising TYLCV resistance conferring alleles on chromosome 6 can be TYLCV resistant wild relatives of tomato, or preferably Solanum lycopersicum plants comprising an introgression fragment on chromosome 6 from such a wild relative of tomato.

The TYLCV resistance phenotype can be tested using a TYLCV resistance assay, either in the field, or in artificial inoculations. Also Ty-1 and/or Ty-3 marker assays can be carried out, in particular when the source of the TYLCV resistance is a S. chilense introgression fragment. Similarly FISH analysis (as described by Verlaan et al. 2011, supra) can be used to show that tomato chromosome 6 comprises an introgression fragment from a wild relative of tomato, said introgression fragment covering at least the region of the long arm of chromosome 6 where Ty-1 and/or Ty-3 is/are found.

Thus, after a cross has been made between a tomato plant having an intense phenotype and a tomato plant having a TYLCV resistance phenotype conferred by an introgession fragment on chromosome 6, a large number of progeny needs to be screened in order to identify the very rare recombinant plant, having both the intense phenotype and the TYLCV resistance phenotype. It is understood that appropriate control plants are preferably included in any such test (field or greenhouse), such as S. lycopersicum plants having an intense fruit phenotype, plants having a normal fruit phenotype (e.g. cv Moneymaker), wild TYLCV resistant plant accessions (e.g. S. chilense LA1969 plants, LA1932 or LA2779 plants) and/or tomato plants having a known TYLCV resistance phenotype (e.g. Ty-1/Ty-1 plants, Ty-3/Ty-3 plants or Ty-1/+ or Ty-3/+ plants) and TYLCV susceptible plants (such as cv Moneymaker). Optionally also a differential host plant set, as described by Lapidot et al. (2006, supra), comprising STY-1. STY-2, STY-4, STY-5 and STY-7 (optionally also STY-3 and STY-6), may be included to determine the level of TYLCV resistance.

Progeny plants can, for example, be of the F2, F3, F4, BC1, BC2, BC1S1, BC1S2, etc. generations. As mentioned above, the intense phenotype is screened by visual assessment of the mature fruits. The TYLCV resistance phenotype can be assessed using different TYLCV resistance assays known in the art and/or using a molecular marker assay. Field assays in white-fly infested areas can be used (see e.g. Examples) and/or artificial inoculations with TYLCV carrying (viruliferous) white flies, as described e.g. by Ji et al. 2007 (supra). As Ty-1 and Ty-3 are partially dominant, it should be noted that the heterozygous presence of these alleles may confer a lower resistance level compared to the homozygous presence. For example Ji et al. 2007 show that plants of the F2 populations comprising Ty-3/Ty-3 have a mean disease severity score of 0.66 (compared to a mean severity score of 2.83 in the susceptible +/+ control), while the Ty-3/+ plants have a mean disease severity score of 1.19.

In either case is the mean disease score statistically significantly lower than the mean disease score of the susceptible control.

Once a progeny plant has been identified which comprises both the intense fruit phenotype and TYLCV resistance, this plant is selected for further analysis and use, for example to generate tomato plants comprising chromosome 6 pairs as shown in FIG. 1. A tomato plant having the intense phenotype and TYLCV resistance can only arise through a rare chromosome cross-over event of homologous chromosomes 6, in between the intense locus and the TYLCV resistance locus. Without such a rare recombination event, plants have either an intense phenotype, but are TYLCV susceptible, or have a normal fruit phenotype and are TYLCV resistant. See FIG. 4 B.

To confirm the coupling in cis, marker analysis can be carried out, FISH analysis and/or co-inheritance of the recombinant chromosome 6 and the intense phenotype (and optionally the TYLCV resistance phenotype) can be confirmed in progeny plants obtained from the selected plant. Also co-inheritance of the two phenotypes (TYLCV resistance and intense fruit phenotype) can be used alone either alone or in combination with e.g. marker analysis. If co-inheritance of the two phenotypes is used to confirm transfer of/presence of the recombinant chromosome 6, one needs to be aware that the intense phenotype is only seen if the intense allele is in homozygous form. The recombinant plant identified as having TYLCV resistance and an intense phenotype initially will have only one copy of the recombinant chromosome 6 (Ty-1/+ intense/intense). Upon selfing, the ratio of plants having both the intense phenotype and the TYLCV resistance phenotype (Ty-1/+ i/i or Ty-1/Ty-1 i/i) to plants having the intense fruit phenotype but no TYLCV resistance (+/+ i/i) is 3:1 phenotypically and 1:2:1 genotypically, i.e. about 25% of progeny plants homozygous for the S. lycopersicum (non-recombinant) chromosome 6, about 50% of progeny plants heterozygous for the recombinant chromosome 6 and about 25% of progeny plants homozygous for the recombinant chromosome 6. Upon crossing the identified recombinant plant with a tomato plant having an intense phenotype (+/+i/i), about 50% of progeny will have an intense phenotype and no TYLCV resistance, while about 50% of progeny plants will have both an intense phenotype and TYLCV resistance due to the inheritance of the recombinant chromosome 6.

"About 25% of plants" and "about 50% of plants" is well understood by the skilled person having knowledge of genetics and heredity as referring to Mendelian segregation of a certain characteristic. In a population of 1000 plants segregating for a certain characteristic in a 1:2:1 ratio, i.e. about 25%:about 50%:about 25% of plants, it is understood that it is not necessary that exactly 250, 500 and 250 plants have the described phenotypes or genotype, but that statistically about 25%, 50% and 25% are of the mentioned phenotypes or genotypes.

In one embodiment marker analysis involves extracting DNA from plant tissue of a plant comprising an intense fruit phenotype and TYLCV resistance, using said DNA as template in a PCR reaction with primer pairs selected from the group of Table 1, preferably using a primer pair detecting at least one marker selected from MSc05732-4, cLEG-31-P16, or a primer pair which can detect any S. chilense DNA in between these two markers, restriction of the amplified DNA with a restriction enzyme as indicate in the Table 1 below, separating the digested DNA fragments on an agarose gel and visualizing the digested fragments under UV light (as known in the art, e.g. as described by Verlaan et al. 2011 or Ji et al. 2007 supra). One or more of these markers can thus be used to determine whether the tomato plant comprises S. chilense DNA (i.e. an introgression fragment from S. chilense) at the marker locus/loci, in order to confirm the presence of the introgression fragment in recombinant plants and optionally the size of the introgression fragment. Obviously, other markers can be developed using methods known in the art or the markers disclosed herein may be detected using different methods or be converted into different markers. The CAPS markers provided can distinguish between homozygous S. lycopersicum DNA, homozygous S. chilense DNA and heterozygous S. lycopersicum/S. chilense DNA at the marker locus. Other markers may thus be any DNA marker which is able to distinguish S. chilense DNA at the marker locus on chromosome 6 from S. lycopersicum DNA. Other markers able to detect S. chilense DNA at or in between marker MSc05732-4 and cLEG-31-P16 may be SNP markers (single nucleotide polymorphism), CAPS markers, SCAR markers, SSR markers or others.

Without limiting the scope of the invention, it is thought that the Ty-1 and Ty-3 alleles lie on the S. chilense DNA region in between markers MSc05732-4 and cLEG-31-P16. Thus, preferably at least marker MSc05732-4 and cLEG-31-P16 (and/or any marker in between) detect S. chilense DNA in plants comprising a TYLCV resistance phenotype and an intense phenotype.

TABLE 1

CAPS markers that can detect S. chilense DNA on chromosome 6

| DNA marker | Primer pair (5'-3') | Annealing temp. | Restriction enzyme | Reference |
|---|---|---|---|---|
| M-H302A23 | tcccgtctcctgcacctacttct (SEQ ID NO: 1)<br>aaaggggtggtgctcgcccct (SEQ ID NO: 2) | 60° C. | HpyF10 VI | Verlaan et al. 2011 (supra) |
| T0774 | ctcctcaactggctaattctcagg (SEQ ID NO: 3)<br>gcaaaccaaatacatcgcgtatcac (SEQ ID NO: 4) | 55° C. | MnI I | Ji et al. 2007 (supra) |
| M-M082G10 | ggcatcgccatcatctctaagtcca (SEQ ID NO: 5)<br>gcctcaacctactgccttgcaaat (SEQ ID NO: 6) | 60° C. | Fsp BI | Verlaan et al. 2011 (supra) |
| MSc05732-3 | atgcttttcgagcacgagcct (SEQ ID NO: 7)<br>agcctaaagagaactaggcagggga (SEQ ID NO: 8) | 55° C. | Rsa I | Verlaan et al. 2011 (supra) |
| MSc05732-4 | acgagatggagcggtcttcaagct (SEQ ID NO: 9)<br>gacagatctcccggtaggagagca (SEQ ID NO: 10) | 55° C. | Dde I | Verlaan et al. 2011 (supra) |

TABLE 1 -continued

CAPS markers that can detect *S. chilense* DNA on chromosome 6

| DNA marker | Primer pair (5'-3') | Annealing temp. | Restriction enzyme | Reference |
|---|---|---|---|---|
| cLEG-31-P16 | atggtgactaaggtggatgagcct (SEQ ID NO: 11)<br>tgagtgccaaccgataatgctacc (SEQ ID NO: 12) | 55° C. | Hae III | Ji et al. 2007 (supra) |
| MSc05732-14 | gtggggcctcgatcccagtca (SEQ ID NO: 13)<br>ggccctttagtgtgtttcacacct (SEQ ID NO: 14) | 55° C. | Nco I | Verlaan et al. 2011 (supra) |

The markers can also be used to transfer a recombinant chromosome 6 (from e.g. a plant having an intense phenotype and TYLCV resistance) into progeny plants, i.e. to select progeny plants for the presence/retention of the recombinant chromosome 6. For example, if one crosses a plant according to FIG. 1 a) or 1c) with a plant having a normal fruit phenotype and lacking TYLCV resistance, about 50% of the F1 progeny will have the recombinant chromosome, while the other (about) 50% will not and none of the plants will have an intense fruit phenotype. The markers, or alternative markers, can thus be easily used in breeding, in order to select plants having a recombinant chromosome 6 according to the invention. However, as already mentioned, phenotypic selection of the intense phenotype and the TYLCV resistance phenotype can equally or additionally be used.

Thus, in one embodiment a tomato plant is provided which comprises a recombinant chromosome 6, comprising the recessive intense gene and an introgression fragment comprising a gene conferring TYLCV resistance in coupling configuration, wherein the introgression fragment comprises a *S. chilense*-genome specific DNA marker selected from the group consisting of MSc05732-4, cLEG-31-P16 or any *S. chilense*-genome specific marker in between these two markers. In one embodiment the tomato plant comprises an intense phenotype and TYLCV resistance and at least *S. chilense*-genome specific marker cLEG-31-P16. In a further embodiment the tomato plant comprises an intense phenotype and TYLCV resistance and at least *S. chilense*-genome specific marker MSc05732-4. In a further embodiment the tomato plant comprises an intense phenotype and TYLCV resistance and at least *S. chilense*-genome specific marker MSc05732-4 and cLEG-31-P16.

In one embodiment the tomato plant comprises an intense phenotype and TYLCV resistance and at least an *S. chilense*-genome specific marker selected from the group consisting of MSc05732-4, cLEG-31-P16 or P16 or any *S. chilense*-genome specific marker in between marker MSc05732-14 and MSc05732-4.

Figure 2:
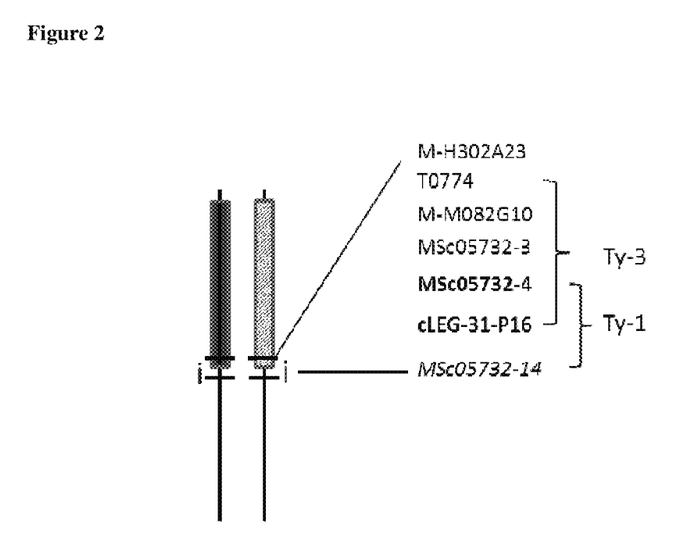
FIG. 2: Schematic illustration of *S. chilense* specific CAPS markers which can be used to detect the presence of a *S. chilense* introgression fragment on chromosome 6 comprising Ty-1 or Ty-3. Adapted from Verlaan et al., Plant J. Vol. 68, Issue 6, p 1093-1103.

As introgression fragments from wild relative of *S. lycopersicum* often also comprise undesired alleles, it is desirable to reduce the introgression fragment as much as possible, while retaining the TYLCV resistance conferring part. Thus, in one embodiment the introgression fragment on tomato chromosome 6 is equal to or less than about 4 Mb, 3 Mb, 2 Mb or 1 Mb in size, preferably equal to or less than 0.8 Mb, such as equal to or less than 0.6 Mb, but still confers TYLCV resistance. In one embodiment the introgression fragment does, therefore, not comprise *S. chilense*-genome specific markers above marker T0774, such as marker M-H302A23 (see e.g. FIG. 2) or others. In one embodiment the introgression fragment does not comprise *S. chilense*-genome specific markers above marker MSc05732-4, such as MSc05732-2, M-M082G10, T0774 and M-H302A23 and other markers further above (further towards the telomere end of the short arm of chromosome 6).

As mentioned above, the existing Ty-1 introgression fragments from LA1969 are very large, about 30 Mb in size. For the existing Ty-3 introgression from LA1932 the introgression fragment is about 27 Mb and for the existing Ty-3 introgression from LA1931 it has been reduced to about 6 Mb (see Ji et al 2007, supra).

In a specific embodiment the recombinant chromosome 6 according to the invention comprises the intense allele in coupling phase with an introgression fragment comprising a TYLCV-resistance conferring allele from a TYLCV resistant *L. chilense* plant, such as LA1969, LA1932 or LA1931, and the introgression fragment is about 30 Mb in size and comprises at least a *S. chilense* genome specific marker selected from the group consisting of T0774, M-M082G10, MSc05732-3, MSc05732-4, cLEG-31-P16 and any *S. chilense* genome specific marker between Msc05732-14 and T0774, or in an alternative embodiment the introgression fragment is significantly less than about 30 Mb in size, such as equal to or less than about 25 Mb, 20 Mb, 15 Mb, 10 Mb, 8 Mb, 7 Mb, 6 Mb, 5 Mb, 3 Mb, 2 Mb, 1.2 Mb 1 Mb, 0.8 Mb, 0.6 Mb and comprises at least a marker selected from the group consisting of T0774, M-M082G10, MSc05732-3, MSc05732-4, cLEG-31-P16 and any *S. chilense* genome specific marker between Msc05732-14 and T0774. But the introgression fragment still comprises the TYLCV-resistance conferring part.

The introgression size can be reduced using known methods, especially by selecting recombinants which retain the TYLCV resistance phenotype, but which lack certain *S. chilense* specific markers. Most simply this is done by starting with a plant comprising a recombinant chromosome 6 according to the invention and then generating and selecting recombinants in progeny generations, which retain the intense phenotype and the TYLCV resistance phenotype, but which comprise a shorter *S. chilense* introgression fragment, i.e. especially *S. chilense*-genome specific markers above marker T0774, or above MSc05732-4, are missing (and *S. lycopersicum* genome specific markers are present instead). Alternatively, one can generate new introgressions, staring from crosses with wild relatives, or one can first reduce the size of existing introgressions and, once one has identified a shorter TYLCV-resistance conferring introgression, one can then cross this plant with a plant having an intense phenotype and select a plant comprising a recombinant chromosome 6 (a plant having both TYLCV resistance and the intense phenotype).

In one embodiment of the invention, a (preferably non-transgenic) *Solanum lycopersicum* plant is provided comprising a TYLCV resistance phenotype and an intense fruit phenotype, wherein said plant comprises at least one recombinant chromosome 6 comprising the recessive intense allele and comprising an introgression fragment originating from a wild relative of tomato comprising an allele conferring TYLCV resistance in coupling configuration, wherein the TYLCV resistance allele is obtainable from a TYLCV resistant *S. chilense* plant, e.g. wherein the TYLCV resistant allele originates from (is the same allele as found in) *S. chilense* accession LA1969, LA1932 or LA1931.

In one embodiment of the invention, a (preferably non-transgenic) *Solanum lycopersicum* plant is provided comprising a TYLCV resistance phenotype and an intense fruit phenotype, wherein said plant comprises at least one recombinant chromosome 6 comprising the recessive intense allele and an introgression fragment originating from a wild relative of tomato comprising an allele conferring TYLCV resistance in coupling configuration, wherein the recombinant chromosome 6 is the recombinant chromosome 6 as found in seeds deposited under accession number NCIMB 41930, or is derived from (obtainable from I can be obtained from) said recombinant chromosome 6. Thus, the recombinant chromosome 6 present in seeds deposited under accession number NCIMB 41930 can be modified further by e.g. reducing the size of the introgression fragment as described above, while retaining the TYLCV resistance conferring part from *S. chilense* and the intense allele from *S. lycopersicum*.

Tomato seeds comprising the recombinant chromosome 6 comprising Ty-1 and the intense allele in cis configuration have been deposited by Nunhems B.V. under accession number NCIMB 41930 on Jan. 27, 2012. Plants grown from these seeds are F1 hybrid tomato plants which produce fruits having the intense phenotype and TYLCV resistance. The seeds deposited are conform FIG. 1 *a*), having a Ty-1/+ intense/intense genotype.

In a further embodiment, seeds and containers comprising seeds from which tomato plants according to the invention can be grown are provided.

Also plants grown from said seeds and having an intense fruit phenotype and TYLCV resistance are provided. The tomato plants may be determinate or indeterminate or semi-determinate. The recombinant chromosome 6 according to the invention can easily be introduced into any tomato plant, any breeding line or cultivar, by crossing and phenotypic and/or marker selection. The intense phenotype and TYLCV resistance phenotype conferred by the recombinant chromosome 6 can thus be combined with other genes and genomes of *S. lycopersicum*. For example, other disease or insect resistance genes, genes for fruit quality characteristics, fruit size, plant or fruit uniformity, plant size, flowering characteristics, fruit shape, taste, stress tolerance, fruit texture, fruit lycopene, beta-carotene or vitamin content, total soluble solids content (brix), long shelf life, etc.

Preferably the tomato plant comprising a recombinant chromosome 6 according to the invention is a cultivated tomato of the species *S. lycopersicum*, i.e. a line or variety yielding high yields, such as fruit of at least 40 or 50 g average fresh weight or more, e.g. at least about 80 g, 90 g, 100 g, 120 g, 150 g, 200 g, 250 g, 300 g, or even up to 600 g (beef tomato types). However, also small types, such as cherry or cocktail tomato are encompassed (having e.g. fruit weights of 30 g or less, such as 25 g, 15 g, 12 g or less). The fruits may be Roma type, cluster type, round, etc. It may be a processing type tomato or a fresh market type. Also both open pollinated and hybrids are encompassed herein. In one embodiment the tomato plant is an F1 hybrid plant, grown from an F1 hybrid seed. In another embodiment the tomato plant is an inbred parent line, suitable as a parent in F1 hybrid seed production. In one embodiment the tomato plant comprises only one recombinant chromosome 6 according to the invention, while in another embodiment the tomato plant comprises two recombinant chromosomes 6 (which may be identical chromosomes or different). The tomato plant may also be a double haploid plant (DH), produced from a cell- or tissue culture of a plant according to the invention, whereby the DH plant comprises two identical recombinant chromosomes 6 of the invention.

Fruits harvested from such tomato plants and comprising a recombinant chromosome 6 according to the invention are also an embodiment of the invention. Such tomato fruits thus have an intense phenotype. The tomato fruits may be of any color (yellow, pink, red, orange, white, purple, black, multicolored, striped, etc.), shape (round, oblong, elongated, pear, etc.) and size (cherry, micro, mini, beefsteak, grape, slicing or globe, plum, pear, etc.). The fruits may be bi-loculate or multi-loculate types. The fruits may be suitable for fresh markets or processing. As the fruits have an intense phenotype, they are particularly suited for sandwiches and salads. Also included are food- or feed products comprising fruits or parts of fruits according to the invention, such as diced fruits, sliced fruits, chopped, fruits, dried fruits, processed fruits (tomato paste, puree, soups, juice, sauces, ketchup, etc.), canned fruits, etc.

In a further embodiment a plant cell, plant tissue or plant part (e.g. a cutting) of a plant according to the invention is provided, which cell, tissue or plant part comprises in its genome at least one recombinant chromosome 6 comprising the recessive intense allele and an introgression fragment comprising an allele conferring TYLCV resistance in coupling configuration. Also an in vitro cell culture or tissue culture of a cell or tissue comprising a recombinant chromosome 6 according to the invention is provided. Plant cells or tissues may be regenerable or non-regenerable into whole plants. Another embodiment provides a tomato plant regenerated from an in vitro cell culture or tissue culture according to the invention, thus comprising a recombinant chromosome 6.

Also vegetatively propagated tomato plants are encompassed herein, for example plants produced from cuttings of a tomato plant of the invention. Tomato plants are easily vegetatively propagated by taking cuttings, allowing these to develop roots and growing a whole plant. The vegetatively propagated plant is genetically identical to the plant part (cutting) which was used to start with.

Further, the use of a (tomato plant or plant part comprising a) recombinant chromosome 6 comprising the recessive intense allele and an introgression fragment comprising an allele conferring TYLCV resistance in coupling configuration for breeding tomato varieties having an intense phenotype and TYLCV resistance is encompassed herein. Traditional breeding techniques can be used to transfer the recombinant chromosome 6 to any other *S. lycopersicum* plant, as already described.

In a further aspect a method of producing *Solanum lycopersicum* plants comprising a TYLCV resistance phenotype and an intense fruit phenotype is provided, said method comprising:

a) providing a tomato plant comprising at least one recombinant chromosome 6 having the recessive intense allele and an introgression fragment comprising an allele conferring TYLCV resistance in coupling configuration, b) crossing and/or selfing said tomato plant with another tomato plant comprising the recessive intense allele, and optionally c) selecting progeny plants comprising the intense phenotype and TYLCV resistance.

In one embodiment the tomato plant under a) may comprises the recombinant chromosome 6 as found in seeds deposited under accession number NCIMB 41930 or a recombinant chromosome 6 derived therefrom. Alternatively, the tomato plants may comprise a different recombinant chromosome 6 as described further above. The TYLCV resistance allele may thus be Ty-1, Ty-3, or an ortholog of Ty-1 or Ty-3. The intense allele is preferably the allele as found in seeds deposited under accession number NCIMB 41930 or in commercial Intense™ varieties. The tomato plant of a) is preferably a line or variety having good agronomic characteristics. Likewise, the tomato plant of b) with which the plant is crossed is preferably a tomato plant having good agronomic characteristics. In c) the progeny plants may be selected phenotypically and/or using DNA markers as described. Steps b) and c) may be repeated one or more times.

In one particular aspect the tomato plant under a) is an inbred plant comprising two identical recombinant chromosomes 6, i.e. the plant is homozygous for the TYLCV resistance allele and is homozygous for the intense allele (e.g. Ty-1/Ty-1, i/i or Ty-3/Ty-3, i/i). This plant is then crossed with a TYLCV susceptible inbred plant which comprises the intense allele in homozygous form (+/+i/i) in step b), in order to produce a F1 hybrid seeds, which when grown into plants are TYLCV resistant and have the intense fruit phenotype. The F1 seeds are collected from said cross and optionally dried. Alternatively, the inbred plant of step b) may also comprising two identical recombinant chromosomes 6 i.e. the plant is homozygous for the TYLCV resistance allele and is homozygous for the intense allele (e.g. Ty-1/Ty-1, i/i or Ty-3/Ty-3, i/i). The F1 hybrid seeds collected from said cross then comprise two recombinant chromosomes 6, one derived from each parent, and the plants grown from said F1 seeds are TYLCV resistant and have an intense fruit phenotype.

In a further aspect a method of introducing a desired trait, such as a TYLCV resistance allele found on another, different chromosome than chromosome 6, into a tomato plant (*Solanum lycopersicum*) comprising a TYLCV resistance phenotype and an intense fruit phenotype is provided, said method comprising:
(a) crossing a tomato plant comprising a recombinant chromosome 6, which comprises the recessive intense allele and an introgression fragment comprising an allele conferring TYLCV resistance in coupling phase, with another tomato plant that comprises one or more desired traits, to produce F1 progeny plants,
(b) optionally selfing the F1 progeny plants one or more times to produce an F2, or F3, or further generation progeny plants,
(c) selecting from said progeny plants those plants that have the recombinant chromosome 6 and the desired trait;
(d) optionally, backcrossing the selected progeny plants with the parent plant of a) (comprising the recombinant chromosome 6) to produce backcross progeny plants;
(e) optionally, selecting for backcross progeny plants that have the recombinant chromosome 6 and the desired trait,
(f) optionally, repeating steps (d) and (e) one, two or more times in succession to produce selected third or higher backcross progeny plants;
(g) optionally, selfing selected backcross progeny in order to identify homozygous plants comprising the recombinant chromosome 6 and the desired trait;
(h) optionally, crossing at least one of said backcross progeny or selfed plants with another parent plant to generate a hybrid variety with the desired trait and an intense phenotype and TYLCV resistance.

The desired trait may be any trait, but is in one embodiment a trait not located on tomato chromosome 6. For example, the desired trait may be the Ty-2 resistance gene found on a *S. habrochaites* introgression fragment on tomato chromosome 11, the Ty-4 resistance gene found on a *S. chilense* introgression fragment on tomato chromosome 3 or the Ty-5 resistance gene found on a *S. peruvianum* introgression fragment on tomato chromosome 4.

The desired trait may be a trait conferring any of the characteristics mentioned further above, such as high brix, disease or insect resistance, fruit shape, color, plant size, flowering characteristics, herbicide resistance, etc. The desired trait may also be a transgenic trait, conferred by a transgene, such as a transgene encoding a *Bacillus thuringiensis* endotoxin or part thereof, a transgene conferring herbicide resistance (against e.g. glufosinate, glyphosate, imidazolinone, triazine, sulfonylurea), etc.

A tomato plant comprising a recombinant chromosome 6 obtainable from (or obtained from) seed deposited under Accession number NCIMB 41930, by crossing NCIMB 41930 with another tomato plant, is also encompassed herein as is the recombinant chromosome 6 as such and its use in generating tomato plants having TYLCV resistance and an intense fruit phenotype.

Also provided is a tomato plant, or part thereof, a representative sample of seeds of which having been deposited under Accession Number NCIMB 41930.

Also provided is a tomato seed, a representative sample of seeds having been deposited under Accession Number NCIMB 41930 and a plant, or a part thereof, produced by growing the seed. In another aspect a progeny plant of tomato variety deposited under Accession Number NCIMB 41930 is provided, obtained by further breeding with said variety, wherein said progeny plant has essentially all physiological and morphological characteristics of the tomato variety (of which seeds have been deposited under NCIMB 41930) when grown under the same environmental conditions.

In yet a further embodiment a transgenic tomato plant (or plant seed, plant cell, plant part) is provided comprising a recombinant chromosome 6 according to the invention and a transgene integrated into the genome.

In another embodiment a transgenic tomato plant (or plant seed, plant cell, plant part) is provided comprising a recombinant chromosome 6 according to the invention, wherein the recombinant chromosome 6, or a part thereof comprising the TYLCV resistance locus and the intense locus in coupling, is introduced into the plant by transformation methods, e.g. by introducing an artificial chromosome or minichromosome into a plant cell and regenerating a whole plant from the cell. See e.g. Lin et al. 2011, Plant Methods 7:10 and Yu et al., Curr Opin Biotech 2007, 18:425-431).

FIGURE LEGENDS

FIG. 1: Schematic illustration of pairs of chromosome 6. Black thin lines illustrate *S. lycopersicum* regions, thick lines illustrate *S. chilense* introgression fragments comprising either Ty-1 (filled) or Ty-3 (striped). The letter "i" refers to the presence of the recessive "intense" allele. All tomato plants comprising a chromosome 6 pair of any one of (a) to (e) are TYLCV resistant and have the intense phenotype. A tomato plant comprising the chromosome 6 pair of (a) is herein also referred to as Ty-1/+ intense/intense (or Ty-1/+ i/i). A tomato plant comprising the chromosome 6 pair of (b) is herein also referred to as Ty-1/Ty-1 intense/intense (or Ty-1/Ty-1 i/i). A tomato plant comprising the chromosome 6 pair of (c) is herein also referred to as Ty-3/+ intense/intense. A tomato plant comprising the chromosome 6 pair of (d) is herein also referred to as Ty-3/Ty-3 intense/intense (or Ty-3/Ty-3 i/i). A tomato plant comprising the chromosome 6 pair of (d) is herein also referred to as Ty-1/Ty-3 intense/intense (or Ty-1/Ty-3 i/i).

"Int" represents the normal allele found in *Solanum lycopersicum*, whereas "i" represents the mutant (recessive) intense allele. In FIG. 4 B, the F2 plants segregate phenotypically in a 1:3 ratio of 1 (intense fruit phenotype, TYLCV susceptible) to 3 (normal fruit phenotype, TYLCV resistant). Only if a rare recombination event (cross over) takes place at a location in between the intense allele and Ty-1 allele is a plant comprising both an intense phenotype and TYLCV resistance produced.

Seed Deposits

A representative sample of seeds of tomato variety comprising a recombinant chromosome 6 were deposited by Nunhems B.V. on 27 Jan. 2012 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 41930.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The following non-limiting Examples describe how one can obtain plants according to the invention, comprising a recombinant chromosome 6. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard breeding methods are described in 'Principles of Plant breeding', Second Edition, Robert W. Allard (ISBN 0-471-02309-4).

EXAMPLE 1

1.1 Materials and Methods 1.1.1 Population Development

Individuals of an inbred *L. esculentum* line comprising two copies of the mutated gene conferring the intense phenotypic trait (i.e. homozygous for intense; belonging to the inbred LH 8587*SR 97180-0-S-3-8) and susceptible to TYLCV, were crossed with a *L. esculentum* hybrid (Hy006, lacking the mutant intense allele) selected in Jordan as resistant to the virus. Resistance was confirmed by molecular analysis to be conferred by the Ty-1 gene, carried in heterozygous form.

Both parents were selected as carrying a similar fruit shape (elongated) and for the determinant plant habit which made it easier to grow progenies in a large number in the open field.

The F1 population was grown in number of 100 individuals, all carrying the mutated intense allele in heterozygous form (thus having a normal fruit phenotype) and segregating for the Ty-1 gene in a ratio of 1:1. The F1 progenies were thus segregating genotypically in a ratio 1 (+/+, I/i):1 (Ty-1/+, I/i).

Using molecular marker analysis 15 individuals were selected from the F1 population which had desired agronomic characteristics and the Ty-1 gene in heterozygous form, so heterozygous for both intense and Ty-1 (Ty-1/+ I/i). These 15 plants were selfed to produce F2 families, each consisting of 150 F2 plants. The 150 F2 individuals were then grown to give a total F2 population of 2250 individuals.

1.1.2 Plant Materials and Growth Conditions

All F2 plants were sowed in a nursery and then transplanted into a breeding field outdoors. Plants were planted according to the local area growing conditions, only at a lower density, spacing 50 cm in the row and 1.40 between rows, in order to make it easier the observation of each single plant (normal density was 40×1.20). Cycle was a typical summer cycle, with transplant in the middle of spring and harvest in mid/late summer. To have two full cycles/year we alternated one growing season in the North hemisphere (South Europe) and one in the South hemisphere (Chile).

The F2 population was screened for intense fruit phenotype and for TYLCV resistance, using molecular marker analysis for Ty-1. One selected F2 individual having TYLCV resistance and intense fruits, supposedly carrying the recombination between Ty-1 and intense, was analysed by molecular markers and self-pollinated to generate F3 individuals, where the recombination between Ty-1 and intense was proven by phenotypic analysis (see 1.1.3 and 1.1.4) and molecular marker analysis (see 1.2).

1.1.3 TYLCV Resistance Analysis of F3 Individuals

Individuals carrying different combinations (homozygous, heterozygous or without Ty-1 gene) for Ty-1 were tested in Aguilas (Spain) in a strongly TYLCV affected area and the reaction to disease was then verified with molecular markers for Ty-1, proving the correlation between marker results for Ty-1 gene and in vivo (phenotypic) TYLCV resistance.

As standard reference commercial hybrids were used. Variety Super Red (Seminis) and NUN 5025 (Nunhems)

were used as TYLCV resistant checks. NUN 6108 (Nunhems), Elliot (Nunhems) and H5656 (Hazera) were used as TYLCV susceptible checks. TYLCV symptoms were scored according to a scale of 0-4, where 0=no symptoms, 1=very slight yellowing, 2=some yellowing and minor leaf curling, 3=significant yellowing and curling, 4=severe yellowing and stunting of plants.

Susceptible checks scored 4, partially resistant checks scored 0.

Selected individuals showing good partial resistance to TYLCV (at the same level of commercial resistant varieties used as checks, i.e. having a TYLCV score=0), proved to carry the Ty-1 gene in homozygous or heterozygous form.

1.1.4 Analysis of Intense Fruit Phenotype

The intense fruit phenotype was determined visually in mature fruits by cutting these open. The seed cavities of the cross-section are compared to the seed cavities of the cross-section of normal fruits of control plants.

1.2 Results

In the F2 population one recombinant plant was found which was TYLCV resistant and had an intense fruit phenotype. Molecular markers showed it was heterozygous for Ty-1 and the fruit phenotype was 'intense'. The recombinant was thus phenotypically TYLCV resistant and produced intense fruits and was genotypically Ty-1/+ I/i.

The recombinant individual plant was selfed to produce an F3 generation and the F3 progenies were planted in the next season (in Spain), to confirm the recombination event.

The F3 progenies segregated in a phenotypic ratio of 'TYLCV resistant and intense' to 'TYLCV susceptible and intense' of 3 to 1. Genotypically, as confirmed by molecular marker analysis, the segregation ratio was 1 (Ty-1/Ty-1, i/i) to 2 (Ty-1/+, i/i) to 1 (+/+, i/i). The observation on the F3 progenies thus confirmed that the selected F2 recombinant plant was homozygous for intense and heterozygous for Ty-1 (Ty-1/+, i/i).

Association of phenotype and confirmation with molecular marker analysis showed that in the F3 population individuals segregated in coupling for Ty-1 and intense, and individuals homozygous for both Ty-1 and intense (Ty-1/Ty-1, i/i) were selected among the F3 progenies.

EXAMPLE 2

Transfer of the Recombination Event into Another Variety 2.1 Materials and Methods The original cross was already involving high value parents. It was decided to go on with the populations homozygous for Ty-1 and intense (above) and do a strong selection using pedigree method to fix possible parent lines to be used directly in hybrid combinations.

At F5 stage the progenies were tested in few combinations to check their combining ability. At F7 stage few lines were fixed and crossed to intense parent lines to generate hybrids to evaluate in screening level.

In particular the progeny LH 56237-15-2-1-3-1-0-10-0 (Ty-1/Ty-1, i/i) was selected, which was crossed with another intense inbred parent line (susceptible to TYLCV) in order to generate the hybrid deposited under accession number NCIMB 41930.

The hybrid and the inbred parents were tested for TYLCV resistance, both under natural infection (exposing seedlings to natural infection and leaving whiteflies free to multiply and infect the plants, even after transplant, throughout the whole trial cycle) and with semi-artificial inoculation (growing viruliferous whiteflies, placing them in contact with seedlings in a netted cage, leaving them to feed each seedling and finally transplanting the seedlings in a protected environment, leaving whiteflies free to further spread the virus).

Both tests were performed in the Nunhems breeding station in Aguilas (Spain), in a strongly TYLCV affected area and each individual plant was scored for TYLCV resistance and intense fruit phenotype. TYLCV symptoms were scored on a scale of 0-4, where 0 indicates symptomless individuals and 4 indicates completely infected non-reproductive plants. As the hybrid is an indeterminate tomato, check varieties were in both tests also indeterminate commercial varieties: variety Anemon (Nunhems) was used as TYLCV resistant check and variety Durinta (Western Seeds) as susceptible check.

2.2 Results

The TYLCV susceptible parent was strongly affected by the virus and did not produce any commercial fruits (having a TYLCV score=4). The homozygous TYLCV resistant parent was free of TYLCV symptoms (TYLCV score=0) and the hybrid NCIMB 41930 was also free of symptoms (TYLCV score=0), producing intense fruits and giving a yield comparable to the commercial resistant varieties.

The invention claimed is:

1. A *Solanum lycopersicum* plant comprising a TYLCV resistance phenotype and an intense fruit phenotype whereby locular gel is replaced by fleshy tissue, wherein said plant comprises at least one recombinant chromosome 6 comprising an intense allele and an introgression fragment comprising an allele conferring TYLCV resistance in coupling configuration wherein said allele conferring TYLCV resistance is a Ty-1 allele from *S. chilense*,
wherein said at least one recombinant chromosome 6 is a recombinant chromosome 6 obtainable from seeds deposited under accession number NCIMB 41930, and wherein said intense allele is the intense allele as found in seeds deposited under accession number NCIMB 41930.

2. The plant according to claim 1, wherein said plant comprises two recombinant chromosomes 6, each comprising an intense allele and an introgression fragment comprising an allele conferring TYLCV resistance in coupling configuration.

3. The plant according to claim 1, wherein said introgression fragment comprises a *S. chilense*-genome specific marker selected from the group consisting of marker MSc05732-4 detectable using PCR primers of SEQ ID NO: 9 and SEQ ID NO: 10 and restriction enzyme Dde I, and marker cLEG-31-P16 detectable using PCR primers of SEQ ID NO: 11 and SEQ ID NO: 12 and restriction enzyme Hae III.

4. The plant according to claim 1, wherein said plant is an F1 hybrid.

5. The plant according to claim 1, wherein said introgression fragment is less than 2 Mb in size.

6. Seed from which the plant according to claim 1 can be grown.

7. A tomato fruit harvested from the plant according to claim 1, wherein said tomato fruit has seed cavities with at least 98% fleshy tissue in the seed cavities.

8. A plant cell, tissue or plant part of the plant according to claim 1 and/or of a seed thereof comprising at least one recombinant chromosome 6 comprising an intense allele and an introgression fragment comprising an allele conferring TYLCV resistance in coupling configuration.

9. A recombinant chromosome 6 comprising an intense allele and an introgression fragment comprising an allele conferring TYLCV resistance in coupling configuration for breeding tomato varieties having an intense phenotype and TYLCV resistance, wherein said allele conferring TYLCV resistance is a Ty-1 allele from *S. chilense*; and wherein said recombinant chromosome 6 is the recombinant chromosome 6 obtainable from seeds deposited under accession number NCIMB 41930.

10. A method of producing *Solanum lycopersicum* plants comprising a TYLCV resistance phenotype and an intense fruit phenotype, comprising:
a) providing a *Solanum lycopersicum* plant comprising at least one recombinant chromosome 6 having the intense allele and an introgression fragment comprising an allele conferring TYLCV resistance in coupling configuration,
b) crossing and/or selfing said tomato plant with another tomato plant comprising the intense allele,
c) selecting progeny plants comprising the intense phenotype and TYLCV resistance
wherein said allele conferring TYLCV resistance is a Ty-1 allele from *S. chilense*;
wherein said at least one recombinant chromosome 6 is a recombinant chromosome 6 obtainable from seeds deposited under accession number NCIMB 41930, and wherein said intense allele is the intense allele as found in seeds deposited under accession number NCIMB 41930.

11. The plant according to claim 1, wherein said introgression fragment is less than 0.6 Mb in size.

12. A *Solanum lycopersicum* plant comprising a TYLCV resistance phenotype and an intense fruit phenotype produced by the method of claim 10.

* * * * *

SEQUENCE LISTING

<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: Forward primer M-H302A23

<400> SEQUENCE: 1
tcccgtctcc tgcacctact tct                23

<210> SEQ ID NO 2

```
<211> LENGTH: 20
<212> TYPE: DNA
<213> ORGANISM: Artificial Sequence
<220> FEATURE:
<223> OTHER INFORMATION: reverse primer M-H302A23

<400> SEQUENCE: 2 aaagggtgg tgctcgccct                                          20

<210> SEQ ID NO 3
<211> LENGTH: 24
<212> TYPE: DNA
<213> ORGANISM: Artificial Sequence
<220> FEATURE:
<223> OTHER INFORMATION: forward primer T0774

<400> SEQUENCE: 3
ctcctcaact ggctaattct cagg                                    24

<210> SEQ ID NO 4
<211> LENGTH: 25
<212> TYPE: DNA
<213> ORGANISM: Artificial Sequence
<220> FEATURE:
<223> OTHER INFORMATION: reverse primer T0774

<400> SEQUENCE: 4
gcaaaccaaa tacatcgcgt atcac                                   25

<210> SEQ ID NO 5
<211> LENGTH: 25
<212> TYPE: DNA
<213> ORGANISM: Artificial Sequence
<220> FEATURE:
<223> OTHER INFORMATION: forward primer M-M082G10

<400> SEQUENCE: 5
ggcatcgcca tcatctctaa gtcca                                   25

<210> SEQ ID NO 6
<211> LENGTH: 24
<212> TYPE: DNA
<213> ORGANISM: Artificial Sequence
<220> FEATURE:
<223> OTHER INFORMATION: reverse primer M-M082G10

<400> SEQUENCE: 6
gcctcaacct actgccttgc aaat                                    24

<210> SEQ ID NO 7
<211> LENGTH: 21
<212> TYPE: DNA
<213> ORGANISM: Artificial Sequence
<220> FEATURE:
<223> OTHER INFORMATION: forward primer MSc05732-3

<400> SEQUENCE: 7
atgcttttcg agcacgagcc t                                       21

<210> SEQ ID NO 8
<211> LENGTH: 25
<212> TYPE: DNA
<213> ORGANISM: Artificial Sequence
<220> FEATURE:
<223> OTHER INFORMATION: reverse primer MSc05732-3

<400> SEQUENCE: 8
```

-continued agcctaaaga gaactaggca gggga 25

<210> SEQ ID NO 9
<211> LENGTH: 24
<212> TYPE: DNA
<213> ORGANISM: Artificial Sequence
<220> FEATURE:
<223> OTHER INFORMATION: forward primer MSc05732-4

<400> SEQUENCE: 9
acgagatgga gcggtcttca agct 24

<210> SEQ ID NO 10
<211> LENGTH: 24
<212> TYPE: DNA
<213> ORGANISM: Artificial Sequence
<220> FEATURE:
<223> OTHER INFORMATION: reverse primer MSc05732-4

<400> SEQUENCE: 10
gacagatctc ccggtaggag agca 24

<210> SEQ ID NO 11
<211> LENGTH: 24
<212> TYPE: DNA
<213> ORGANISM: Artificial Sequence
<220> FEATURE:
<223> OTHER INFORMATION: forward primer cLEG-31-P16

<400> SEQUENCE: 11
atggtgacta aggtggatga gcct 24

<210> SEQ ID NO 12
<211> LENGTH: 24
<212> TYPE: DNA
<213> ORGANISM: Artificial Sequence
<220> FEATURE:
<223> OTHER INFORMATION: reverse primer cLEG-31-P16

<400> SEQUENCE: 12
tgagtgccaa ccgataatgc tacc 24

<210> SEQ ID NO 13
<211> LENGTH: 21
<212> TYPE: DNA
<213> ORGANISM: Artificial Sequence
<220> FEATURE:
<223> OTHER INFORMATION: forward primer MSc05732-14

<400> SEQUENCE: 13
gtggggcctc gatcccagtc a 21

<210> SEQ ID NO 14
<211> LENGTH: 24
<212> TYPE: DNA
<213> ORGANISM: Artificial Sequence
<220> FEATURE:
<223> OTHER INFORMATION: reverse primer Msc05732-14

<400> SEQUENCE: 14
ggccctttag tgtgtttcac acct 24